United States Patent
Shih et al.

(10) Patent No.: US 6,177,068 B1
(45) Date of Patent: Jan. 23, 2001

(54) VINYL AMIDE POLYMER DELIVERY SYSTEM FOR HAIR AND SKIN TREATING COMPOSITIONS

(75) Inventors: Jenn S. Shih, Paramus; Jui-Chang Chuang, Wayne; Krystyna Plochocka, Scotch Plains, all of NJ (US)

(73) Assignee: ISP Investments Inc., Wilmington, DE (US)

( * ) Notice: Under 35 U.S.C. 154(b), the term of this patent shall be extended for 0 days.

(21) Appl. No.: 09/203,910

(22) Filed: Dec. 2, 1998

Related U.S. Application Data

(63) Continuation-in-part of application No. 08/988,121, filed on Dec. 10, 1997.

(51) Int. Cl.$^7$ .............................. A61K 7/06; A61K 7/00
(52) U.S. Cl. ..................... 424/70.17; 424/59; 424/70.12; 424/70.15; 424/70.9; 424/78.02; 526/263; 526/264; 526/307.1; 526/307.3
(58) Field of Search ................................. 424/401, 70.17, 424/70.15, 70.12, 70.9; 526/194, 307.1, 264

(56) References Cited

U.S. PATENT DOCUMENTS

| | | | | |
|---|---|---|---|---|
| 5,130,121 | * | 7/1992 | Kopolow | 424/47 |
| 5,189,102 | * | 2/1993 | Tsubuko | 525/112 |
| 6,022,547 | * | 2/2000 | Herb | 424/401 |

* cited by examiner

*Primary Examiner*—Fred Zitomer
(74) *Attorney, Agent, or Firm*—Marilyn J. Maue; William J. Davis; Walter Katz

(57) ABSTRACT

A cosmetically active oil-in-water (o/w) or water-in-oil (w/o) emulsion, for topical applications comprising (a) the reaction product of a non-aqueous, heterogeneous polymerization of a liquid reaction mixture containing between about 5 and about 70%, preferably 10–40%, by weight, of N-vinylamide monomer in an oil solvent, a free radical initiator, between about 0.1 and about 2.5% by weight of a crosslinking agent and optionally a surfactant, (b) water sufficient to form said emulsion, (c) a cosmetically active hair and/or skin treating chemical or chemical composition and optionally (d) a surfactant.

9 Claims, No Drawings

VINYL AMIDE POLYMER DELIVERY SYSTEM FOR HAIR AND SKIN TREATING COMPOSITIONS

This application is a continuation-in-part of Ser. No. 08/988,121, filed Dec. 10, 1997, assigned to the same assignee as herein.

BACKGROUND OF THE INVENTION

1. Field of the Invention

This invention relates to controlled-release, cosmetically active topical delivery systems for improved hair and skin anti-pollutant and anti-aging films as well as moisturizing and sunscreening effects by controlled release of cosmetically active components or formulations of said components.

2. Description of the Prior Art

In the industry directed to hair and skin treating compositions extensive research has been devoted to improving and extending the effectiveness the active hair and skin components used in topically applied formulations. Gradual and controlled release of active sunblocking, moisturizing and anti-pollutant protective films, lotions, creams and solutions is particularly of interest to the industry. Also, the retention or extended release of fragrances contained in such formulations or in perfumes and colognes is of some interest. Heretofore inexpensive and effective methods have evaded research. Accordingly, the present invention is specifically directed toward viable methods for prolonged release of topically applied cosmetically active ingredients in treatments for hair and skin thereby in creasing the overall desired effectiveness at smaller active concentrations while additionally improving the storage stability of formulations containing such active components. It is also the aim of this invention to reduce the number of separate topical applications required over an extended period to achieve a desired cosmetic effect.

In addition to the above advantages, it is also an object of the invention to provide a pH and salt tolerant thickener for a wide range of existing cosmetically active formulations having a neutral or acidic pH.

These and other objects and features realized by the use of the present invention will become apparent from the following disclosure.

SUMMARY OF THE INVENTION

In accordance with this invention there is provided a cosmetically active, delivery medium in the form of an o/w or w/o emulsion composition for topical application to the hair or skin which contains (a) the liquid polymerization product obtained from reacting the mixture of between about 5 and about 70%, preferably 10–40%, by weight of N-vinyl amide monomer in a hydrophobic solvent, a free radical initiator and between about 0.1 and about 2.5% by weight of a polyfunctional crosslinking agent, (b) water sufficient to form said emulsion, (c) a cosmetically active hair and/or skin treating chemical or chemical composition and optionally (d) a surfactant.

DETAILED DESCRIPTION OF THE INVENTION

The crosslinked N-vinylamide polymers of this invention are derived from monomers which include linear and branched aliphatic vinylamides containing from 3 to 8 carbon atoms and N-vinyl lactams containing 4 or 6 ring carbon atoms which can be mono- or di-substituted with a $C_1$ to $C_4$ alkyl group. Preferred amide polymers of this group are the crosslinked polymers derived from said N-vinyl lactam or mixtures of said lactams, most particularly those derived from N-vinyl pyrrolidone (VP). Specific examples of other suitable monomers include N-vinyl methylpyrrolidone, N-vinyl ethylpyrrolidone, N-vinyl caprolactam (VCPL), N-vinyl methylcaprolactam, N-vinyl formamide, N-vinyl acetamide, N-vinyl butylamide, N-vinyl propyl amide, N-vinyl isopropylamide, N-vinyl 3-ethyl hexylamide and the like.

The crosslinked polymers herein defined can be prepared by the anhydrous precipitation polymerization of N-vinylamide monomer with a cosmetically acceptable, hydrophobic solvent in the presence of between about 0.1 and about 2.5 wt. % based on monomer of an innocuous crosslinking agent. Throughout the polymerization/crosslinking reactions, the monomer solvent, preferably an oil, also acts as a medium to maintain the crosslinked polymer product in a stirrable liquid state. The reaction product is generally recovered as a slurry; however, if desired, the reaction product may be filtered to provide the crosslinked polymer as a powder swollen with oil. Thereafter, the resulting polymer slurry or powder swollen with oil is homogenized with water to form a uniform liquid emulsion or gel which is directly useful as a thickening agent or as a carrier for an active hair and/or skin treating chemical or a preformed formulation containing the cosmetic chemical along with minor amounts of conventional cosmetic excipients, such as for example, a coloring or fragrance additive, a separate solvent, a surfactant, a foaming agent and the like.

Generally between about 5 and about 70%, preferably 10–40%, by weight, of amide monomer reactant is used in the process, and about 30–95 wt. % of the oil is included to maintain solubilization of the system. The cosmetically active components of this invention include known hair and skin conditioners, emolliating and moisturizing agents such as hydroxy-substituted $C_8$ to $C_{50}$ unsaturated fatty acids and esters thereof, $C_1$ to $C_{24}$ esters of $C_8$ to $C_{30}$ saturated fatty acids such as isopropyl myristate, cetyl palmitate and octyl-dodecylmyristate (Wickenol 142), beeswax, saturated and unsaturated fatty alcohols such as behenyl alcohol and cetyl alcohol, hydrocarbons such as mineral oils, petrolatum, squalane, fatty sorbitan esters, lanolin and lanolin derivatives such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot or peach pits, walnuts, palm nuts, pistachio nuts, sesame seeds, rapeseed, cade oil, corn oil, poppyseed oil, castor oil, soybean oil, avacado oil, grapeseed oil and sunflower seed oil and $C_1$ to $C_{24}$ esters of dimer and trimer acids such as diisopropyl dimerate, diisostearylmalate, diisostearyldimerate and triisostearyltrimerate. Also suitable are moisturizing agents such as decyl oleate, diisopropyl adipate, octyl palmitate glycerin or their formulations in suitable non-irritating solvents; anti-aging film forming agents, e.g. those containing liposomes; chemically active sunscreens, such as octyl dimethoxycinnamate and octyl dimethyl p-amino benzoic acid; depigmentation agents, e.g. hydroquinones; hair cleansing or relaxing agents; hair dyes and lighteners; makeup removers, e.g. chloroacetamide; depellicating agents and anti-wrinkle, anti-aging agents such as α-hydroxy carboxylic acids, particularly lactic acid, glycolic acid, α-hydroxy propionic acid, α-hydroxybutyric acid, as well as acid containing polymers such as poly(methyl vinyl ether/maleic acid) and poly(methyl vinyl ether/acrylic acid) copolymers. Mixtures of the above active components can also be employed as the active component in the present compositions.

The amount of active component incorporated in the emulsion product can vary widely depending upon the active species selected, the desired affect, the solubility in the emulsified polymer carrier and irritability to the skin. Of the active components described above, the α-hydroxy carboxylic acids are most preferred.

To form the cosmetically active emulsion product of this invention, the total amount of the active component can be introduced during the homogenizing step with water. Alternatively, it can be introduced with vigorous agitation after the emulsion has been formed.

Suitable hydrophobic solvents employed in this invention are silicone oils or fluids selected from non-volatile silicones, such as polyalkyl siloxanes, polyaryl siloxanes, polyalkylaryl siloxanes and polyether siloxane copolymers; however, volatile silicones such as cyclomethicones are also suitable. The non-volatile polyalkylsiloxanes include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes is from about 100 to about 100,000 cps, and most preferably, about 200 to about 15,000 cps. Specific examples of the non-volatile polyalkylaryl siloxanes include, for example, poly(methylphenyl)siloxane having viscosities of from about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenyl-siloxane) copolymers having a viscosity in the range of about 10 to 100,000 cps at 25° C. are useful. These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Other suitable oils for use herein include pharmaceutically-acceptable materials such as light and heavy mineral oils, low vapor pressure isoparaffins e.g., (Isopar M and Isopar V solvents, supplied by Exxon Chemical) and water-insoluble organic esters such as isopropyl palmitate and isopropyl myristate and liquid petroleum or waxy oils.

The polymerization process is effected with a free radical initiator which is preferably introduced before and during the polymerization reaction. If desired, the polymerization can be initiated at a relatively low temperature and then at a higher temperature as the reaction progresses toward completion. The same initiator can be employed throughout reaction or a higher temperature initiator can be used for the high temperature stage. Suitable free radical initiators include diacetyl peroxide, dibenzoyl peroxide, dilauroyl peroxide, t-butyl peroxypivalate, t-butyl peroctoate, 2,5-dimethyl-2,5-bis(t-butylperoxy)hexane (LUPERSOL 101), t-amyl peroxypivalate, di-(4-t-butylcyclohexyl) peroxydicarbonate, 2,2'-azo-bis(isobutyronitrile), 2,2'-azo-bis(2,4-dimethyl-valeronitrile), and 1,1'-azo-bis(cyanocyclohexane), as well as mixtures thereof.

Useful crosslinking agents for the present lactams, preferably present in the reaction mixture at a concentration of from 0.3 to 2 wt. % based on monomer, include such multifunctional compounds as α-, ω-allyl ether of alkanes, divinyl ethers of an aliphatic diol, e.g. the divinyl ethers of α-, ω-$C_3$ to $C_{12}$-alkanediols; as well as divinyl ethers of di-, tri-, tetra-, penta-ethylene glycols and the like. Other suitable crosslinking agents include α-, ω-$C_8$ to $C_{14}$ dienes, divinylbenzene, N,N-divinylimidazolidone, allyl ether derivatives of polyhydric alcohols such as pentaerythritol triallyl ether (PETA), triallyl-1,3,5-triazine-2,4,6(1H,3H,5H)-trione(TATT), diallylimidazolidone, 2,4,6-triallyloxy-1,3,5-triazine, ethylene glycol diacrylate, N-vinyl-(E)-ethylidene pyrrolidone (EVP), methylene bis(N,N-acrylamide), methylene bis(methacrylamide), ethylidene bis(N-vinylpyrrolidone) (EBVP), hexaallyl sucrose, and the like and mixtures thereof.

The surfactant, although not required, can be employed in the reaction mixture to augment stabilization of the desired emulsion and gel products. When employed, an oil soluble surfactant is added to the polymerization reaction mixture; whereas a water soluble surfactant can be employed during the water homogenization stage. The amount of surfactant in either stage is between about 0.5 and about 10%, preferably between about 1 and about 5%, based on oil present. Suitable oil soluble surfactants useful for polymerization include, but are not limited to, cetyl dimethicone copolyol (Abil® EM-90, product of Goldschmidt Chemical Corp.); Span® 80 (ICI) and Dow Corning 3225 silicone. Water soluble surfactants which can be employed are described hereinafter.

In the practice of the present invention, a cosmetically acceptable hydrophobic solvent, eg. an acceptable oil, is charged into a reactor, under agitation and a blanket of nitrogen and heated to between about 40° and about 150° C., preferably between about 60° and about 75° C., after which the free radical initiator, generally at a concentration of from about 0.001 to about 0.01 wt. %, based on monomer, is added. Thereafter vinylpyrrolidone (VP) and crosslinking agent are introduced continuously over a period of from about 1 to about 12 hours, preferably a period of from about 3 to about 6 hours. Optimally, as indicated above, the vinyl monomer and crosslinking agent feed into the reactor is adjusted to a rate such that practically no free monomer phase is present during the polymerization.

After polymerization is complete, the polymer is obtained as an oil slurry. The slurry can be used as is or filtered to remove excess oil, resulting in the product consisting of solid polymer with significant amount of absorbed oil. Both slurry and filtered polymer are useful in the formation of the present o/w and w/o cosmetic product.

The products made herein may be easily converted into emulsions or emulsified hydrogels which contain the crosslinked polymer in the aqueous phase. The emulsion can be an o/w or a w/o type. The oil droplets obtained can be dispersed in a continuous aqueous hydrogel phase (o/w). Conversely, when oil is a continuous phase, and water swollen polymer hydrogel is dispersed in oil, the system generated is w/o emulsion. Both are formed under vigorous agitation.

The selected ratios of oil-to-water in such emulsions and emulsified hydrogels are predetermined by the desired use compositions; these can be adjusted within a broad range. Typically, oil-to-water ratios for the o/w emulsions reside within the range of about 30:70 to about 10:90 by volume. In corresponding w/o systems, the ratios of oil-to-water are suitably within the range of about 90:10 to about 65:35 by volume.

When an o/w emulsion system is desired, the oil/ crosslinked polymer is gradually added to water beneficially containing a water soluble surfactant with appropriate rapid agitation or homogenization. Preferred water soluble surfactants which are optionally added to these systems, include for example, Tween® 20, 21, 40, 61 (ICI) or Igepal® CO-630(product of Phone-Poulenc), Span® 60, 65, 80, 85 (ICI) or Dow Corning® 3225C formulation. The oil soluble surfactant added optionally to the polymerization reaction mixture also may be used to form the desired aqueous emulsion or emulsified hydrogel.

EXAMPLE 1

106.25 g of poly(dimethylsiloxane) silicone oil (Dow Corning 200® Fluid), having a Brookfield viscosity of 130 cps, is charged into a 1-liter glass resin kettle and heated to 65° C., while sparging with nitrogen followed by the addition of 0.05 g of t-butyl peroxypivalate (Lupersol® 11, 75% active, Elf Atochem). Thereafter 18.75 g of N-vinylpyrrolidone (VP) monomer is continuously fed into the reactor over a period of 3 hours and 0.083 g of triallyl-1,3-triazine-2,4,6(1H,3H,5H)-trione (TATT) crosslinking agent is introduced. A booster shot of 0.05 g Lupersol® 11 is added after initiation of reaction and the reaction continued for another 2 hours after which another booster of 0.05 g Lupersol® 11 is added and the reaction continued for another 1 hour. The resulting product is the crosslinked polymer in silicone oil.

EXAMPLE 2

Into a 1-liter, 4-necked resin kettle, fitted with an anchor agitator, a nitrogen purge adapter, a thermometer, two subsurface feeding tubes connected with two feeding pumps, and a reflux condenser, 800 g of 5 cps silicone oil is charged. Nitrogen purging is started and continued throughout the subsequent reaction. Agitation at 200 rpm is also maintained throughout the process. To the reactor contents heated and maintained at 65° C., 520 microliter of t-butyl peroxypivalate (Lupersol® 11) is charged followed by the gradual addition of 200 g of N-vinylpyrrolidone and 0.90 g of pentaerythriol triallyl ether crosslinker over a period of 6 hours. After another 30 minutes the reaction mixture is transferred to a 2-liter high pressure reactor and 1 g of 2,5-dimethyl-2,5-bis(t-butyl-peroxy)hexane (Lupersol® 101) initiator is charged into a sealed reactor, heated to 120° C. where reaction is completed over a period of 8 hours. The resulting product, i.e. crosslinked PVP/silicone oil slurry (35 g), is then vigorously mixed with 65 g of water to provide the o/w emulsion.

Similar results are obtained when N-vinyl caprolactam monomer or N-vinyl formamide is substituted for N-vinyl pyrrolidone in the above example.

EXAMPLE 3

The process of Example 2 is repeated except that 5 g of cetyl dimethicone copolyol (Abil® EM-90) surfactant is added with initiator in the polymerization stage. The reaction product, i.e. the resulting polyvinylpyrrolidone in silicone oil slurry with surfactant, is recovered. To the above slurry (35 g), 32 g of silicone oil is introduced and 5.0 g of lactic acid in 33 g of water is then added dropwise during the homogenization, thus providing the w/o controlled release of lactic acid in the emulsion carrier which is the desired product of this invention.

EXAMPLE 4

Example 3 is repeated and 5.0 g of α-hydroxy propionic acid is added during the water homogenizing step to provide the controlled release of the α-hydroxy propionic acid in the o/w emulsion carrier of the invention.

EXAMPLE 5

A 1-liter resin kettle is charged with 205 g of Dow Corning 200® Fluid silicone oil, sparged with nitrogen and, under constant agitation, heated to 65° C., after which 0.25 g of Lupersol® 11 is added. Thereafter, a mixture of 36 g of N-vinylpyrrolidone, 0.16 g of triallyl-1,3,5-triazine-2,4,6-(1H,3H,5H)-trione (TATT) as crosslinker and 0.72 g of Span® 80 surfactant is added over 6 hours, with two additions of 0.25 g each of Lupersol® 11 after 3 and 6 hours. The reaction is continued for an additional 1 hour and the resulting reaction slurry cooled and filtered to yield 123 g of a waxy crosslinked PVP precipitate containing about 75% silicone oil. This precipitate is then homogenized with gradual addition of 300 g of water and then with another 300 g of water to produce an o/w emulsion. This emulsion is suitable for the addition of the cosmetically active component.

EXAMPLE 6

Example 3 is repeated except thar 5.0 g of octyl dimethoxy cinnamate is added to the reaction mixture during the water homogenizing step to provide a sunscreening affect to the o/w emulsion.

EXAMPLE 7

Example 3 is repeated except that 5 g of maleic acid/ methyl vinyl ether copolymer is added to the reaction mixture during the homogenizing step to provide an acid containing o/w emulsion.

What is claimed is:

1. The process for producing the cosmetically, controlled-release active emulsion of a crosslinked N-vinyl amide polymer which comprises:

(a) precharging into a reactor under an inert gas atmosphere and anhydrous conditions, at a temperature of between about 45° C. and about 150° C. an oil solvent in an amount sufficient to maintain the subsequent reaction mixture in the liquid state, (b) adding thereto an effective polymerization promoting amount of a free radical initiator, (c) gradually adding over a period of from about 0.5 to about 8 hours with constant agitation, between about 5 and about 70 wt. % N-vinylamide monomer and between about 0.1 and about 2.5 wt. %, based on monomer, of a polyfunctional crosslinking agent for said N-vinylamide monomer and initiating the polymerization of said monomer, (d) continuing said polymerization until not more than 1% of unreacted monomer remains in the reaction mixture, (e) adding water to (d) in an oil to water volume ratio concentration of between about 10:90 and about 90:10 under agitation sufficient to homogenize the aqueous mixture and form a stable emulsion and (f) adding an effective hair or skin enhancing amount of said cosmetically active agent, optionally in the presence of a surfactant, to the aqueous mixture under constant agitation until a uniformly distributed composition is obtained.

2. The process of claim 1 wherein the cosmetically active agent is selected from the group consisting of an α-hydroxy carboxylic acid, a UV absorber and a carboxylic acid containing copolymer of methyl vinyl ether and maleic or acrylic acid.

3. The process of claim 2 wherein said carboxylic acid is selected from the group consisting of carbonic acid, glycolic acid, α-hydroxy propionic acid, α-hydroxy butyric acid, lactic acid and mixtures thereof.

4. The process of claim 1 wherein said monomer is N-vinyl pyrrolidone and wherein an initial polymerization of the monomer is effected at a temperature of between about 45° and 70° C. and polymerization is subsequently continued at a higher temperature.

5. The process of claim 4 wherein a low temperature polymerization initiator is employed in said initial stage of polymerization and a higher temperature polymerization initiator is employed in said subsequent stage.

6. The process of claim 5 wherein said low temperature initiator is t-butyl peroxypivalate and said higher temperature initiator is 2,5-dimethyl-2,5-bis(t-butylperoxy)hexane.

7. The process of claim 1 wherein said oil solvent is a silicone oil.

8. The process of claim 1 wherein the crosslinking agent is selected from the group consisting of an α-, ω-divinyl ether of an alkane; a divinyl ether of a di-, tri-, tetra- and penta-ethylene glycol; divinyl benzene; N,N-divinyl imidazolidone; an allyl ether of a polyhydric alcohol; ethylene glycol diacrylate; N-vinyl-(E)-ethylidene pyrrolidone; methylene bis(acrylamide); methylene bis (methacrylamide); ethylidene bis(N-vinylpyrrolidone) and mixtures thereof.

9. The process of claim 1 wherein an oil soluble surfactant is added to the reaction mixture prior to the introduction of the monomer.

* * * * *